United States Patent [19]

Ebert

[11] Patent Number: 5,127,413
[45] Date of Patent: Jul. 7, 1992

[54] SINOUS SUTURE

[76] Inventor: Edward A. Ebert, 203 Huxley Dr., Snyder, N.Y. 14226

[21] Appl. No.: 564,794

[22] Filed: Aug. 9, 1990

[51] Int. Cl.⁵ ............................................ A61B 19/00
[52] U.S. Cl. ........................................ 128/898; 606/103
[58] Field of Search .................... 606/228, 232, 103; 24/205, 27, 548, 549, 550, 567; 128/898; 140/71 C; 411/16, 392

[56] References Cited

U.S. PATENT DOCUMENTS

| | | | |
|---|---|---|---|
| 672,977 | 4/1901 | Cronenberger | 24/27 |
| 731,008 | 6/1903 | Wyckoff | 24/567 |
| 1,224,062 | 4/1917 | Boor | 24/27 |
| 1,372,629 | 3/1921 | Osley | 24/27 |
| 2,274,699 | 3/1942 | Jacobs | 140/71 C |
| 2,582,093 | 1/1952 | Ayers | 24/27 |
| 2,956,474 | 10/1960 | Holzwarth et al. | 24/27 |
| 4,146,022 | 3/1979 | Johnson et. al. | 606/103 |
| 4,590,929 | 5/1986 | Klein | 606/103 |
| 4,622,960 | 11/1986 | Tam | 606/103 |
| 4,901,721 | 2/1990 | Hakki | 24/27 |

Primary Examiner—Stephen C. Pellegrino
Assistant Examiner—Gary Jackson

[57] ABSTRACT

A suture for binding fractured bone parts together, when placed around a bone, to enhance regrowth and healing of the bone. The suture comprises a resilient monofilament material having continuously occurring contact areas uniformly separated from each other by non-contacting spaces to permit the continuity of blood vessels nerve channels, body fluids or other body parts from one side of the suture to its other side when the suture is under tension around a bone or cartilage.

1 Claim, 6 Drawing Sheets

SINOUS SUTURE

BACKGROUND OF THE INVENTION

This invention relates to a suture which can be used for binding together, separated, splintered and fractured bone parts, or as in the case of chest surgery, to bring together the severed sternum in exact alignment in a fixed relationship.

As expressed in my U.S. Pat. No. 4,535,764, prior wire ties are unsatisfactory in that they can cut the bone that they bind when used in smaller gauge diameters and also leave sharp ends to break through the skin cover. Other devices as shown in U.S. Pat. Nos. 3,125,095; 4,549,545; 4,896,668; 4,119,091; 4,201,215; 4,279,248 and 4,263,904 are also deficient in many respects in that they are bulky, either do not have proper binding or cause too much tightness with a tourniquet effect. Furthermore, prior wire sutures choke off blood vessels and other channels and create more trauma than that already there to hinder the healing process.

SUMMARY OF THE INVENTION

In surgery and where bones are broken or cut apart, a suture used to sew or bind parts together exerts pressure on on those parts. This, many times causes a tourniquet effect which cuts off the flow of blood to the parts on opposite sides of the suture, thereby starving parts of needed blood for healing. It is an intent and purpose of this invention to alleviate the choking of blood and nerve channels with the attendant obviating of the added trauma and stress and thereby enhance faster healing.

It is an object to provide a suture with a proper binding capability in spite of the fact that it obviates complete choking of body parts on opposite sides of the suture.

Another object is to provide the suture with a capability of attaining a tightness up to a certain predesigned limit, but not over said limit so that the surgeon performing the surgery can go about his work knowing that there is not an excess of tightness or looseness.

A still further object is to provide a suture that can be handled easily with a surgeon's regularly used tools such as forceps, needle holders and hemostats.

Further, it is an object to provide a suture which is as small in cross section as is consistent with its desirable qualities and which has enough of a bearing surface to prevent cutting the bone.

A further object is to provide a suture which has a great deal of flexibility to fit in close conformity to undulating and irregular surfaces.

Other objects and attendant advantages will readily be perceived hereafter when the following portions of the specification are read in conjunction with the accompanying drawings wherein:

BRIEF DESCRIPTION OF THE DRAWINGS

FIG. 1 is a cross-sectional view of a fractured bone with a corrugated type of suture installed and wrapped around its perifery under tension holding the fractured parts together;

FIG. 1A is a fragmentary cross-sectional view similar to FIG. 3 through a suture in a sternum that it has been threaded through;

FIG. 2 is an enlarged fragmentary side elevational view of a prior art monofilament.

FIG. 3 is a cross-sectional view taken along line 3—3 of FIG. 2;

FIG. 14 is a side elevational view of a corrugated suture made of the flattened monofilament of FIG. 11;

FIG. 15 is a cross-sectional view taken along line 15—15 of FIG. 14;

DESCRIPTION OF THE PREFERRED EMBODIMENTS

In the drawings, FIGS. 1-15 are provided to encompass quickly the relationship of several basic forms of this invention, compared with present practice, to highlight their unique advantages over the present form of suture used. These figures also compare the tread widths w and the aggregate masses of material of the various forms.

Figures 1, 1A, 2, 3:
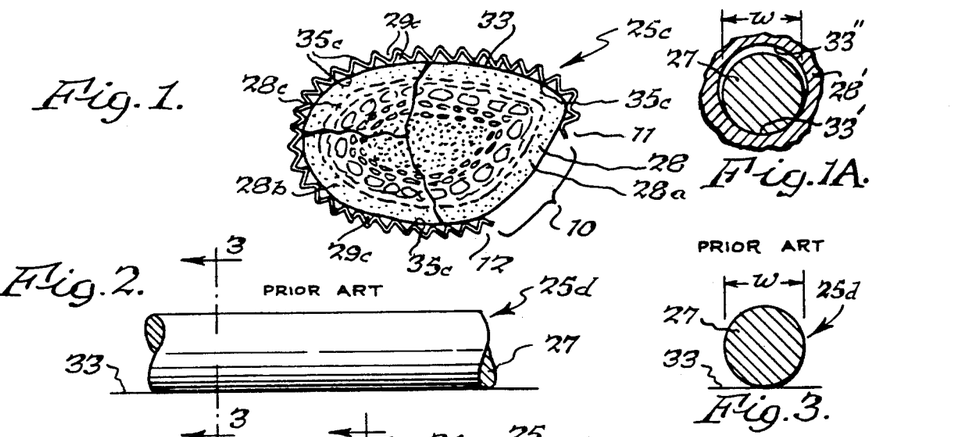

The present invention is shown in FIG. 1 in the form of a corrugated suture 25c surrounding a fractured bone 28, and it is in tension when placed around the bone 28, which tension converts into inward radial pressure to press the bone parts 28a, 28b and 28c together for healing. The bracket at 10 indicates where a form of locking means (not shown) would lock the two ends 11 and 12 of the suture 25c together to maintain the linear tension in the suture.

As can readily be seen in FIG. 1 the suture 25c has corrugations which form contact areas 35c and void spaces 29c therebetween.

The contact areas 35c provide a wide footing w, as seen in FIG. 15, which will not cut through soft bone or cartilage 33 while at the same time the voids or spaces 29c provide unchoked areas at or near the surface 33 for free passage of blood, body fluids or nerve continuity from one side of the suture to its other side. The surface 33 is not only unfettered and free but below its surface, it is relatively uncompressed and without stress. This is in contrast to the prior art monofilament suture, 25d shown in FIGS. 2 and 3 which is solid and smooth and acts as a tourniquet to cut through when of small cross-sectional area, choke off the bone at the surface and within it any of the surface or sub-surface channels for communications such as blood vessels and nerve continuity, creating further trauma in tissue which should be guarded from further stress to enhance its healing.

The prior art 25d is what is currently being used in chest surgery to reclose a sternum. The overall diameter of the monofilament is about 0.035 inches and it has a tread width w as shown in FIG. 3.

The term, tread width w, as used herein, is interpreted as meaning, the full width contact 33' of a suture 27 in a perforation 33" that it has been threaded into, such as in a sternum 28', as shown in FIG. 1A or its contact on the surface around a bone 28 that it would tend to crush and perforate through excessive force, as in FIG. 1.

All of the following forms of the invention illustrated in basic form in the FIGS. 3-15 are shown as having a substantially identical size tread width w for purposes of comparison.

Figures 4, 5, 6:
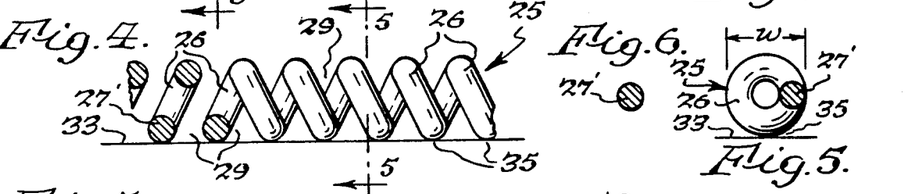
FIG. 4 is a fragmentary side elevational view partially in cross-section of a helically coiled monofilament suture.
FIG. 5 is a cross-sectional view taken substantially along line 5—5 of FIG. 4.
FIG. 6 is a cross-sectional view of the monofilament used in the coiled suture of FIG. 4.

A form of the invention is shown in FIGS. 4 and 5 as a continuous helix of coils 26 one after another, wound to the same outside diameter and having the same tread width w as that in FIGS. 2 and 3. It is wound of the same surgical stainless steel monofilament, but its filament is about one third of the cross-sectional diameter of 0.012" D. instead of 0.035" D. as that shown in FIG. 3.

Figure 4A:
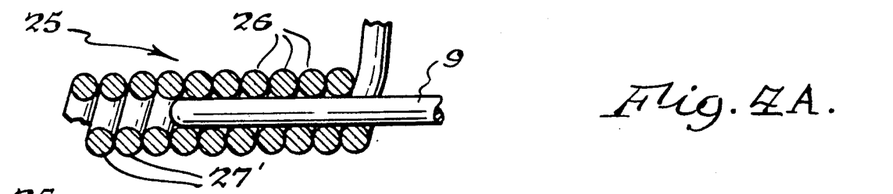
FIG. 4A is a fragmentary cross-sectional view showing a monofilament wound onto a mandrel.

Sutures such as 25 in FIG. 4 can be made in the following manner. A monofilament 27' is tightly wound onto a mandrel 9 as seen in FIG. 4A so that each of the coils 26 touch one another or are in close proximity to each other. After a sufficient length is wound, the mandrel 9 is removed from the wound suture 25 and it is stretched beyond its elastic limit so that when relaxed the spaces 29 will be approximately the size of the monofilament 27' as seen in FIGS. 4 and 6.

This suture 25 will now have an approximate mass of about only one eight and one half of that shown in FIG. 3 and a tensile strength of 32 pounds while the tensile strength of the 0.035" D. suture 25d shown in FIGS. 2 and 3 amounts to approximately 240 pounds. It is believed that this suture strength is much stronger than that needed since the sternum bone would pull apart and splinter at much less than a 240 pound pull. Therefore, that size suture diameter indicated and shown as prior art in FIGS. 2 and 3 must have been chosen for its tread width w to prevent cutting of the bone, not, for its tensile strength.

It would appear that a tensile strength of 32 pounds is more nearly in the range of the strength needed for binding a sternum, since in most cases a minimum of six sutures which would give a total strength of 6×32 pounds equalling a total of 192 pounds. For very large persons eight sutures would be used giving a total of 256 pounds strength.

Figures 7, 8:
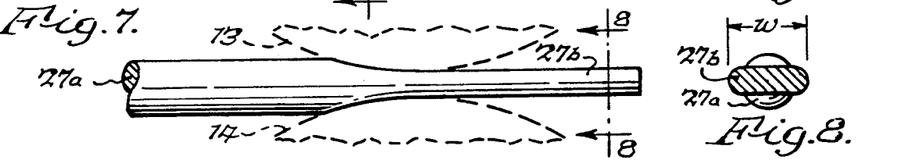
FIG. 7 is a fragmentary elevational view of a monofilament wire being flattened between upper and lower rolls shown in dotted lines of a rolling mill.
FIG. 8 is a cross-sectional view taken along line 8—8 of FIG. 7, cutting through the reduced flattened section.
Figures 7A, 9A:
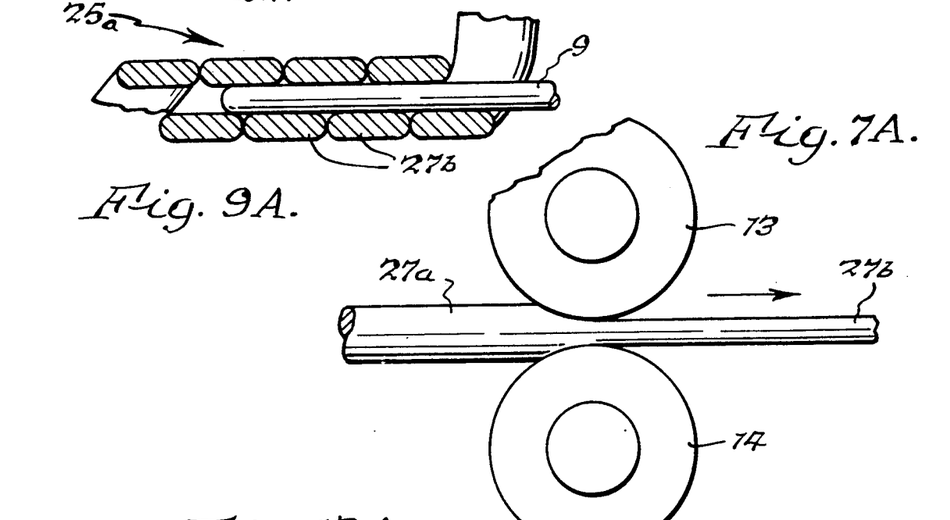
FIG. 7A is a fragmentary view of the rolling mill with a suture wire shown along its length.
FIG. 9A is a fragmentary cross-sectional view showing a flattened monofilament wound onto a mandrel.

As shown in FIGS. 7, 7A and 8, a suture wire 27a of about 0.024" D. is being flattened by mill rolls 13 and 14 to a flattened ribbon monofilament 27b having a cross-section of 0.012" thick by approximately 0.036" wide and having a tensile strength of approximately 124 pounds.

Figures 9, 11:
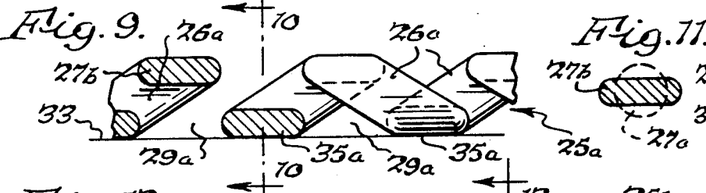
FIG. 9 is a side elevational view, with parts in cross-section, of the flattened monofilament shown in the section of FIG. 8, wound into a helix of continuous coils.
FIG. 11 is a cross-sectional view of the monofilament which is coiled into the helical coils of FIGS. 9, 9A and 10.
Figure 10:
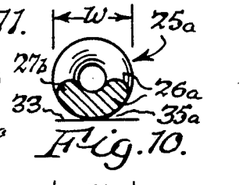
FIG. 10 is a cross-sectional view taken along 10—10 of FIG. 9.

FIGS. 9, 9A and 10 show a helically wound suture 25a fabricated of this ribbon 27b shown in cross-section in FIG. 11. As seen in FIG. 9 the part shown in section shows the monofilament cross-sections as being long in the direction of the lineal length of the suture 25a. This feature gives this particular suture much greater lineal resistance to stretch and also a much wider pitch or wind.

This suture 25a shown being wound in FIG. 9A on a mandrel 9 is made in an identical manner to that of the suture 25 in FIG. 4A and will not be repeated.

Figures 12, 13:
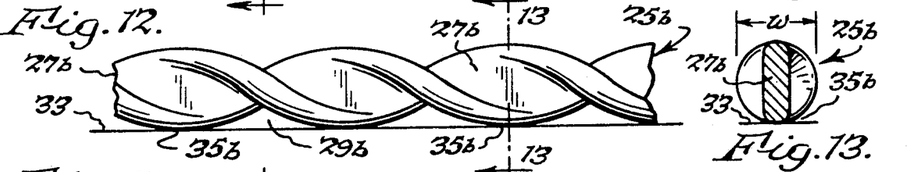
FIG. 12 is a twisted version of the flattened monofilament cross-section shown in FIG. 11.
FIG. 13 is a cross-sectional view taken along line 13—13 of FIG. 12.
Figure 12A:
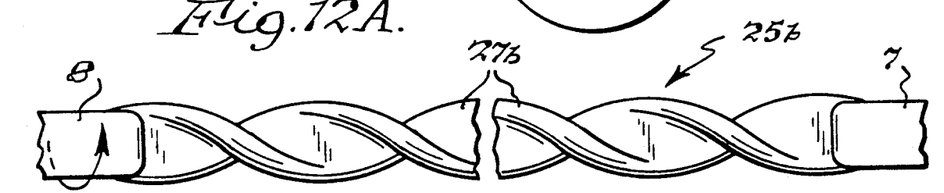
FIG. 12A is an elevation of the means used to twist a flattened monofilament.

In FIGS. 12 and 13 is shown a flattened ribbon suture 27b as seen in FIG. 11 which has been twisted into a continuous screw-like suture 25b by the means shown in FIG. 12A. In this respect, the suture ribbon 27b may be chucked in the stationary jaws 7 to the right of FIG. 12A while the left end is chucked in the jaws 8. Rotations of the jaws 8 then twist the suture into its screw-like configuration beyond its elastic limit to whatever amount of twist that is desired.

Figure 14A:
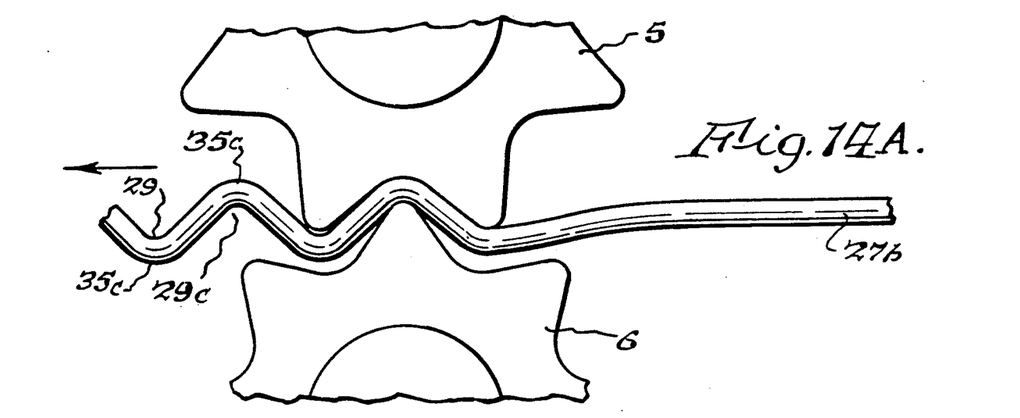
FIG. 14A is a side elevational view of a flattened monofilament being corrugated.

In FIGS. 14 and 15 a flattened ribbon suture 27b has been corrugated into ridges 35c or contact points or areas and grooves or spaces 29c. The manner of corrugating is shown in FIG. 14A where a pair of corrugating rolls 5 and 6 have properly shaped teeth and sockets to form the flat ribbon 27b into the ridges or contact points 35c alternating with the grooves or spaces 29c.

As can now readily be seen all four forms 25, 25a, 25b and 25c have basic similarities. Each having a monofilament body 27, 27' and 27b, each have contact points 35, 35a, 35b and 35c, each have spaces 29, 29a, 29b and 29c, and each have less aggregate mass than the suture 27 shown in FIGS. 2 and 3.

All of the foregoing embodiments now have a lineal elasticity and each have a similar tread width w. The less aggregate mass and cross sectional area of each embodiment makes for greater lateral flexibility. Each embodiment also provides less bone cutting potential because of the wide tread width w. In addition each embodiment has the aforementioned advantage of permitting free passage of flows and nerve continuity from one side to the other of the suture. All of these sutures can be interspersed, one into the other for maintaining a tension in the suture. Those in FIGS. 4-13 will intersperse on any side by side relationship 360° around the suture's diameter such as above or below or side by side with the exception of the ribbon form shown in FIGS. 1, 14, 14a, 15 and 41-47. This ribbon form 25c is limited for interlocking or nesting, only, by being under the inner bone contacting side of the suture or by being over the outer side of the suture.

When external forces act upon a material, they produce tension, compression, bending, shearing, or torsional stresses within the material. In most instances, a combination of two or more of these stresses are produced. All stresses to which a material is subjected cause a deformation in it. If the stress is not too great, however, the material will return to its original shape and dimensions when the external stress is removed. The property which enables a material to return to its original shape and dimensions is called -elasticity-. If a material has been stressed to such an extent that, upon removal of the load; it does not fully return to its original shape and dimensions its -elastic limit- has been exceeded.

Since the -elastic limit- is a basic and inherent quality of the material composite in a suture, used in each individual class of use and cannot be changed once alloyed and manufactured, this invention proposes to provide a means to vary this quality by the way it is made into a suture.

The means used to accomplish this result is to use a lever arm, either long or short in effect, in applying a torsion, tension or compression to the material in the suture.

In a coiled suture this lever arm is related to the outside diameter of the coil. If the coil diameter is small the lever arm is short.

In a twisted form this lever arm is dependent on the largest flat wise dimension in the twist.

In the coil and twisted form it is torsion that is affected while in the corrugated configuration it is bending, tension and compression that is affected Thus by lengthening the lever arm (enlarging the coil size) the suture is softer in -elasticity- and the monofilament reaches its -elastic limit- with a lesser amount of stress on the suture but with a longer stretch. Also by shortening the lever arm (reducing the coil size) the suture is stiffer in -elasticity- and the monofilament reaches its -elastic limit-with a greater or increased amount of stress required in a much shorter stretch. This same relationship occurs in the corrugated form where the material between reverse corrugation bends form a lever arm between the bends while at the same time it functions as a short leaf spring. Again the longer the arm the softer the -elasticity- and the -elastic limit- is reached with a lesser amount of stress. With a shorter arm the reverse is true.

In all forms coiled, twisted or corrugated the closer the pitch, the softer the suture and wider the pitch the stiffer the suture. Also in all forms, these characteristics, in this invention are related to the size and number of the bone contact and non-contact spaces between.

Further, to altering material characteristics of the suture, is the temper of the material used. Some can be tempered as is a well known practice today. On the other hand in manufacturing, manipulation of a material can cause it to work harder to an undesirable hardness when in finished form. If a soft ductile suture is desired, it is proposed to accomplish annealing of the suture in a simple precise and controllable manner by using its electrical resistance to cause heating of the monofilament up to a controlled temperature. By connecting electrical current to the extremities of the suture and timing its application until an annealing temperature is reached and then cooling it slowly.

Figures 16, 17, 18, 19, 20:
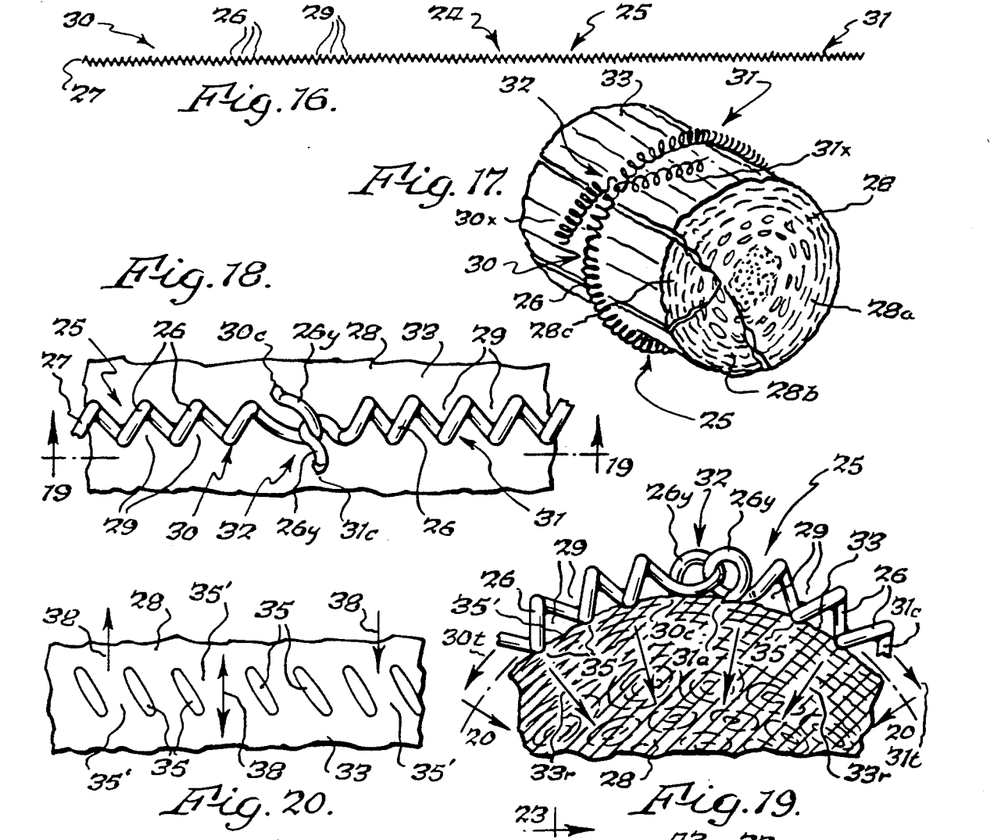
FIG. 16 is an elevational plan view of a helical coil suture before installation.
FIG. 17 is a view in perspective of a segment of columnar bone with a suture holding its fragmented parts together.
FIG. 18 is an enlarged fragmentary plan view of an installed suture of the type of FIG. 4 with its two ends hooked together and trimmed.
FIG. 19 is a fragmentary cross-sectional view taken along line 19—19 of FIG. 18.
FIG. 20 is a fragmentary plan view of the contact tread that the suture of FIGS. 18 and 19 would leave impressed upon the bone surface and is taken along line 20—20 of FIG. 19.

Suture 25 of FIGS. 16–26 is shown as a continuous helically wound coil 26 with its turns spaced from each other by spaces 29. It may be fabricated of surgical stainless wire 27 or suitable plastic monofilament. The suture 25 has a first end portion 30, a middle portion 24 and a second end portion 31. As seen in FIG. 17 the suture 25 is shown as binding together a fragmented bone 28 which was fractured longitudinally into three parts 28a, 28b and 28c. Also in this view the first end 30 and the second end 31 of the suture have been hooked together by being bent back around each other at 32 after the suture 25 has been tensioned around the fragmented bone. The portions 30x and 31x which are subsequently bent back are originally grasped to position the suture 25 around the bone and to pull it to the desired tension. Thereafter the ends 30x and 31x are bent back around one another to hook a single coil 26, as shown in FIG. 18 to provide a secure fastening. The ends 30x and 31x are thereafter trimmed very close, as at 30c and 31c and shown in FIGS. 17, 18 and 19. However it should be noticed in FIGS. 17, 18 and 19 that the suture wire is wound in a counter clockwise rotation, i.e. in a left hand wind, as in a left hand screw thread, with the ends 30x and 31x, FIG. 17 brought together in a counter clockwise bend, i.e. a counter clockwise twist. This causes the hooked coils 26 to terminate their cut ends 30c and 31c close to and pointing downwardly toward the bone surface 33 to obviate jagged ends which may penetrate the skin surrounding the bone as seen in FIG. 19.

Conversely to that just described a clockwise wound suture and a clockwise twist will cause the cut off ends 30c and 31c to point upwardly away from the bone surface creating two skin tearing points 30c and 31c to snag and break through the tissue that will cover the suture. This would require a cover to guard against breaking through the skin as will be explained later.

The hook-up just described is simple, easy to manipulate with fingers or forceps and without slippage or loss of tension, for several reasons. (1) The close spacing of each coil 26 is a very small increment distance relative to the elasticity of the suture, so that a correct hook-up point for proper tension in the suture is always close by. (2) Any individual coil 26 inserted into a coil space 29 spreads the space to enter it and then it falls in between two of the coils 26. (3) The ends 30x and 31x are hooked about each other as shown in FIG. 17, to form a secure hook-up.

In the cross sectional view shown in FIG. 19 the suture 25 exerts a radial inward force on the bone surface 33 as indicated by the arrows 33r because of the tension in the suture 25 indicated by arrows 30t and 31t.

The surface 33 of the bone 28, shown as a plan view in FIG. 20 shows the tread or footing contact 35 made by the coils 26 contacting the surface 33. It can be seen that these treads 35 provide a large distribution of inward pressure to preclude any surface cutting of the bone 28 at the contact points 35. Further, these treads 35 are oblique to the longitudinal axis of the bone and they are spaced from each other to provide the spaces 35' therebetween. The arrows 38 indicate the flow path between spaces 35' for body fluids or nerve continuity proximate the bone surface 33.

In the past, one method of suturing a bone has been by the use of a soft non-elastic ductile wire wrapped about the bone with its two ends twisted together to tighten the suture around the fractured or splintered parts. If the tie was too loose the fractures were not brought together properly and if it was too tight the outer surface could be crushed or cut by the small diameter of the wire and also the flow of body fluids proximate above and below the surface of the bone was cut off. In heart surgery where cutting of the sternum is required, the bone being quite porous and soft can be easily cut by the wire which then allows the suture to become loose. Hence an over size wire is used there. Also the wire acts as a tourniquet and can cut off the passage of blood, body fluids and nerve channels. Since bone has on its surface and slightly below many connections of various sorts, choking these off not only prevents faster healing but adds more trauma to the original trauma caused by the cutting or fracture of the bone.

The present invention alleviates the foregoing unfavorable characteristics by the fact that the various sutures such as 25, 25a, 25b and 25c are elastic and can be designed for a certain use and thus they produce a proper tension to keep them tight around the bone surface 33. Each suture of the foregoing type cannot crush or cut the bone 28 because of its large and distributed tread and it cannot be applied with too great a tension at the time of installation because when the elastic limit of the monofilament is reached it will elongate above a certain tension and will not exceed it. This means that the suture can be designed with an elastic limit making any cutting or crushing of the bone impossible and yet can be custom designed for a stiff or soft resilience. Thus by using a customized suture a surgeon can concentrate on getting the closing done without fear of over or under tightening. Further as can be seen from FIGS. 19 and 20 the tread 35 or footing is generally crosswise of the suture 25 length thus providing the spaces 35' to provide flow passages in the direction of the arrows 38 in FIG. 20.

Figures 21, 22, 23, 24:
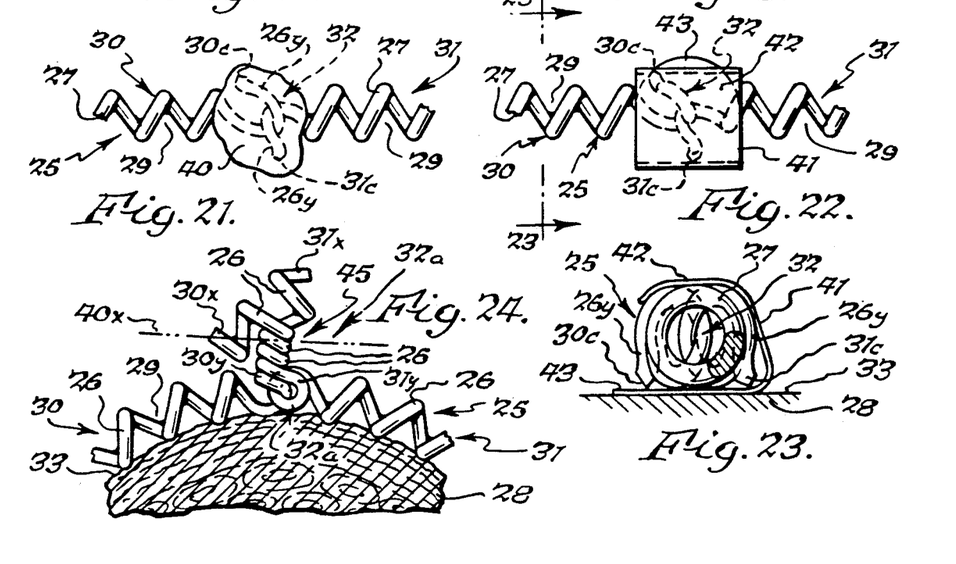
FIG. 21 is a plan view similar to that of FIG. 18 with the hooked coil ends embedded in a matrix material.
FIG. 22 is a similar view with the hooked coils covered by a clip.
FIG. 23 is a cross-sectional view taken along line 23—23 of FIG. 22 showing how the clip embraces the hooked coils.
FIG. 24 is a cross-sectional view showing the hooked coils being further entwined together in a manner similar to current practice.

In FIG. 21 is shown a covering for the hook-up point 32. This covering is in the form of a matrix or blob 40, which could be any thick encapsulation such as hot silicone melt, epoxy resin putty or other, as long as it is surgically acceptable. The covering 40 should cover any sharp projections of the hook-up 32 and aid in maintenance of its security.

FIGS. 22 and 23 show another form of protector for the hooking juncture 32 and comprises a generally C shaped clasp 41 of thin flexible material. This clasp 41 has a smooth top cover part 42 connected to a flat base 43 and is slipped over the hook-up 32 with its base part 43 wedged between the suture 25 and the bone surface 33 after the excess ends 30x and 31x have been cut off. The tension of the suture 25 on the bone 28 and the spring of the clasp 41 around the suture 25 is sufficient to hold it in place.

Another form of hook-up 32a is illustrated in FIG. 24 wherein the hook-eyes 30y and 31y are shown as being twisted several times by the bent back portions 30x and 31x creating a twisted stem 45, which makes for a hook-up 32a that is very secure. The stem 45 may be cut off at the cut line 40x to reduce bulk and then bent down to lay along the bone surface 33.

Here again it should be noted that the direction of the twist of the stem 45 relative to wind of the coil 26, left hand or right hand is important. If the suture 25 is a left hand wind as shown in all of the FIGS. 16-23, the stem 45 should be twisted in a right hand (clockwise) direction for a close tight twist as shown in FIG. 24 with the coils 26 intermeshing with one another. If twisted in a counter clockwise (left hand) direction the coils 26 and spaces 27 do not intermesh and the coils 26 are uncoiled and then recoiled into an uneven knotty stem.

Successful examples of the foregoing sutures 25 have been made using surgical stainless wire 0.011" in diameter having a tensile strength of 27 pounds wound closely over a 0.013" diameter mandrel which results in a coiled suture having an outside diameter of 0.039". This prewound suture 25 is then stretched to elongate the suture to one having spaces or voids 29 to the same dimension as the wire size. Other wires 0.016" in diameter have been wound to an outside diameter of 0.069". Also plastic monofilament of 0.035" in diameter wound to a diameter of 0.070" has been used. These examples are mentioned for better understanding of the invention and are not to be considered as parameters of limitation.

To custom design these sutures 25 for a particular use which might vary from small finger bones to femur bones and larger, as well as sternums it is necessary to have some with soft elasticity and others much stiffer, plus a certain elastic limit that is built in. The elastic limit and elasticity of sutures 25 can be varied in several ways. (1) By using different materials with greater or lesser tensile strength. (2) By winding coils or corrugating with greater or lesser number of coils or corrugations. (3) By winding larger size coils or making larger corrugations for softness and smaller coils or corrugations for stiffness. (4) Also an increase or decrease in monofilament of ribbon thickness or width will increase or decrease the elastic limit. (5) Wire hardness will also increase the elastic retaining ability of the suture.

Figures 25, 26, 27, 28, 29, 34:
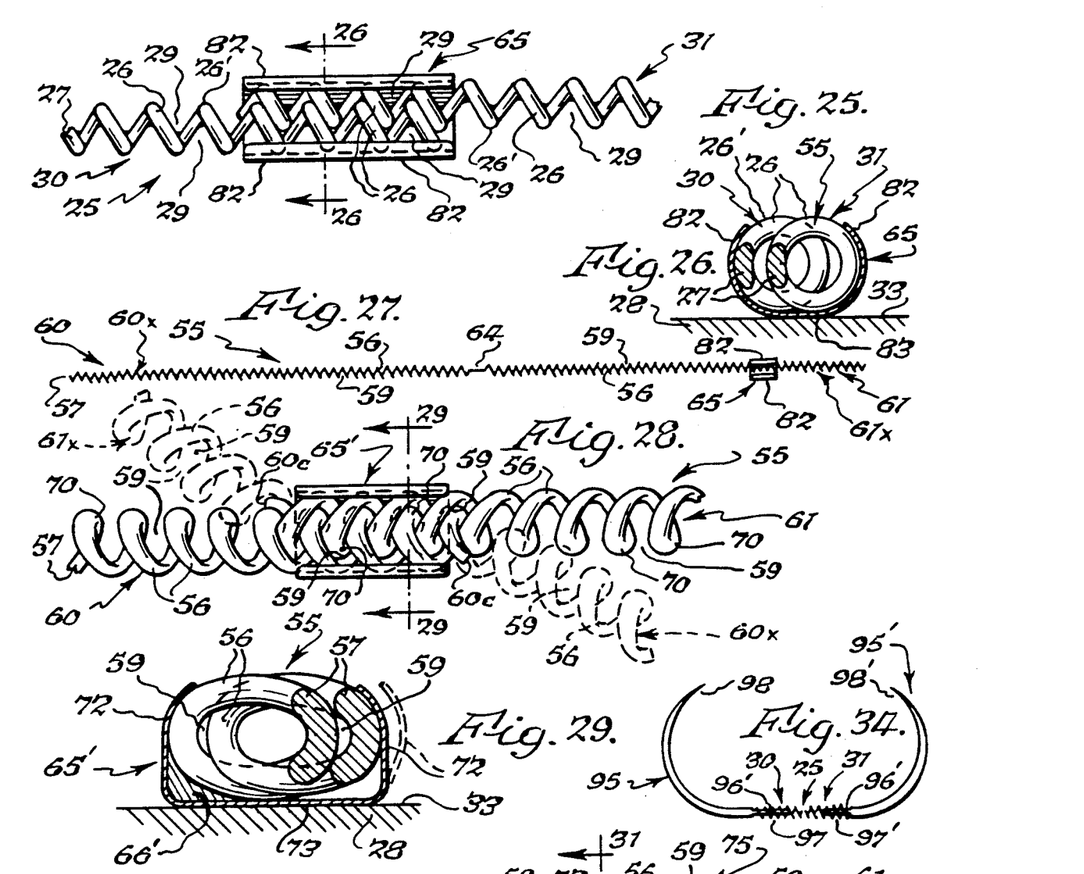
FIG. 25 is a fragmentary plan view of a suture being held in a side by side interfacing engagement by a spring clip.
FIG. 26 is a cross-sectional view taken along line 26—26 of FIG. 25.
FIG. 27 is an elevational plan view of another form of suture having one end coiled clockwise and its other end coiled counter clockwise with both ends connected to each other by a middle portion and with one of the ends carrying a clasp.
FIG. 28 is an elevational view of the form shown in FIG. 27 wherein the clockwise and counter clockwise ends intersperse with each other, aided for engagement together by a clip.
FIG. 29 is a cross-sectional view taken along line 29—29 of FIG. 28.
FIG. 34 is a fragmentary view of a suture of any of the foregoing types including a curved needle at each of its ends.

A suture 25 shown in FIGS. 25 and 26 may be used with a retaining keeper 65 which will keep and maintain the first end 30 and the second end 31 in an interposed relationship. As seen in FIG. 25 when the ends 30 and 31 are tensioned and layed side by side so that the outside faces 26' of the coils 26 lay into the spaces 29 they have a somewhat shallow interposing relationship. This interposition is not self-maintaining with the suture 25 under tension so that a keeper 65 is required to hold the two ends, 30 and 31 together in a locking engagement.

The keeper 65 comprises a base portion 83 with two upstanding flexible curved side walls 82 and may be fixed to either of the ends 30 or 31 in any suitable manner. This keeper could also be inverted with the base 83 being used as a cover for the retainer.

A form of the invention shown in FIG. 27 comprises a bone suture 55 of continuous helically wound coils 56, each spaced by spaces 59 and made of surgical metallic wire 57 or suitable plastic monofilament. A first end portion 60 is wound in one direction while its second end portion 61 is wound in an opposite direction both being joined by a middle portion 64. A clasp 65 may be fixed to either of the ends 60 or 61 in such position as to provide finger pieces 60x and 61x.

The purpose of opposite winds of the ends 60 and 61 is that when they are layed alongside each other they will intersperse into each other, in a much deeper association than that described before, wherein the wind of all of the coils was in only one direction. In right and left hand winding the coils 56 fit into the spaces 59 more deeply like a screw thread fits into its matching nut.

In FIGS. 28 and 29 a suture wound left and right hand such as 55 is made of plastic monofilament and it has coils 56 and spaces 59. These spaces 59 are slightly narrower than the diameter of the monofilament 57 so that when the coils 56 are forced together they have an interference fit with each other. A slight force is required to bring each of the coils 56 into the spaces 59 but when they are together they resist separation. By making them into an oval configuration as seen in the sectional view of FIG. 29 and with an enlargement area 70 along one side of each of the coils 56 as seen in FIG. 28 they tend to grab into a tighter locking when placed under tension. The clasp 65' in this case is used for engaging the two ends 60 and 61 side by side and is not needed to maintain the locked condition but can be used to align and guide the interspersing.

Figures 30, 31, 32, 33:
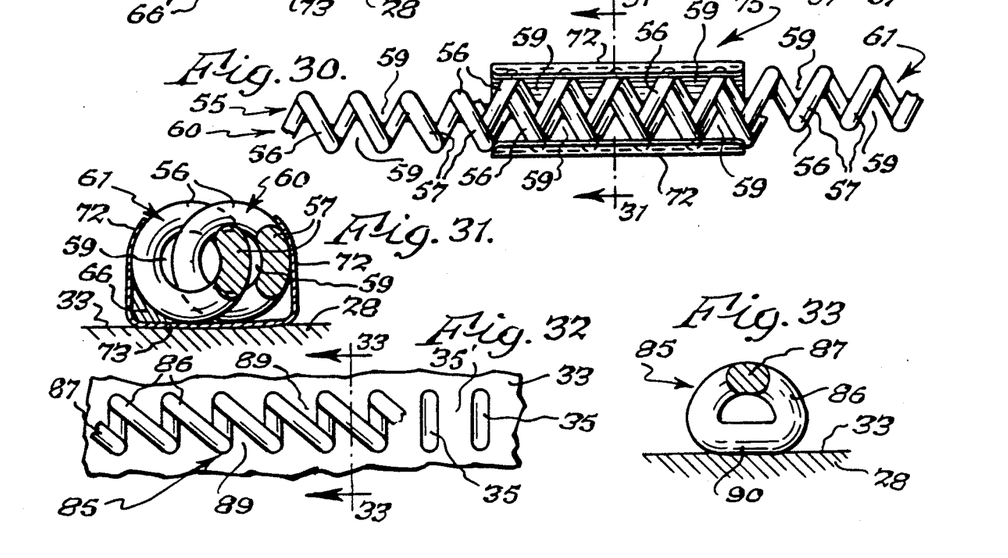
FIG. 30 is a fragmentary plan of a form of the embodiment of FIG. 27 having a loosely interspersed fit with a clasp to maintain the locking ends interspersed with each other.
FIG. 31 is a cross-sectional view taken along 31—31 of FIG. 30.
FIG. 32 is a fragmentary plan view of another form of the invention having a flattened bone contacting side, lateral to the sutures lineal axis.
FIG. 33 is a cross-sectional view taken along line 33—33 of FIG. 32.
Figure 35:
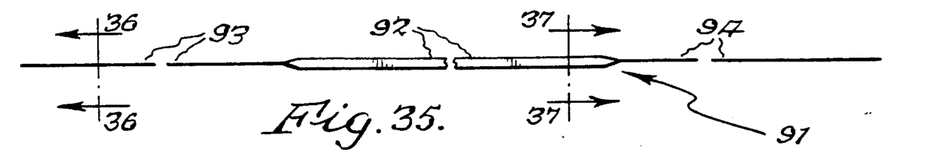
FIG. 35 is a plan view of a length of suture monofilament having each of its ends of round cross section connected by a middle portion of flattened cross section.

The invention form shown in FIGS. 30 and 31 comprise a suture 55 as shown in FIG. 27 and having monofilament 57 of a diameter smaller than the dimensions of the spaces 59, making a very loose intermesh. This construction then requires a keeper 75 to maintain a locking together of the coils 56 in the spaces 59. Keeper 75 has curved walls 72 and a base 73.

In FIGS. 32 and 33 a special D shaped coil 86 is shown having a treat 35 and a flow space 35' at right angles to the lineal centerline of the suture 85 of a monofilament 87, the tread 35 is provided by the bottomside 90 of the coil 86 and gives this suture a large wide bearing on the bone surface 33.

The rejoining of a cut sternum in chest surgery is usually done in the following manner; the needle of a suture is entered into one side of the sternum from the outside and then exits at the inside. A space exists between the two cut edges of the sternum so that a surgeon has enough room to clamp onto the needle tip with a needle holder and draw the suture into a slack loop. The needle is then entered into the other side of the sternum from the inside of the chest cavity and then is maneuvered to exit at the outside. The needle is then broken off and the suture is used to draw the split parts of the sternum together whereupon the ends are locked together. The foregoing usual mode of operation is deficient because the needle which descends downwardly may accidentally pierce an internal organ.

The construction in FIG. 34 may be provided with a curved needle 95 having a point 98 and a reduced shank 96 which is entered into the bore of the coil 26 where it is fixed at 97.

A second needle 95' having a point 98' at the other end 31 of the suture 25 by a reduced end 96' and fixed thereto at 97' as shown in FIG. 34 would provide an advantage of greater safety and accurate placement if used in the following manner as described in detail in my copending application Ser. No. 476,582, filed Feb. 7, 1990.

Since as mentioned, a gap exists between the two cut edges of the sternum, the joining of the edges would be done with the structure of FIG. 34 by inserting the needle 95 into the underside of one part of the sternum from the inside to the outside and then doing the same, with the needle 95' on the other part of the sternum, from the inside to the outside of the sternum, thus preventing any accidental penetration of organs inside the chest cavity because downward needle movement is eliminated. Needles 95 and 95' are then cut off and the sternum halves pulled together by the suture and the suture ends 30, 31 are suitably fastened together making the closure complete, to maintain a pressure on the surfaces of the cut preventing further bleeding and encouraging healing. This procedure also reduces the length or amount of a suture that must be drawn through the needle perforations in the sternum. With the use of only one needle the whole length of the suture must be pulled through the first needle perforation.

Figures 36, 37, 39, 40:
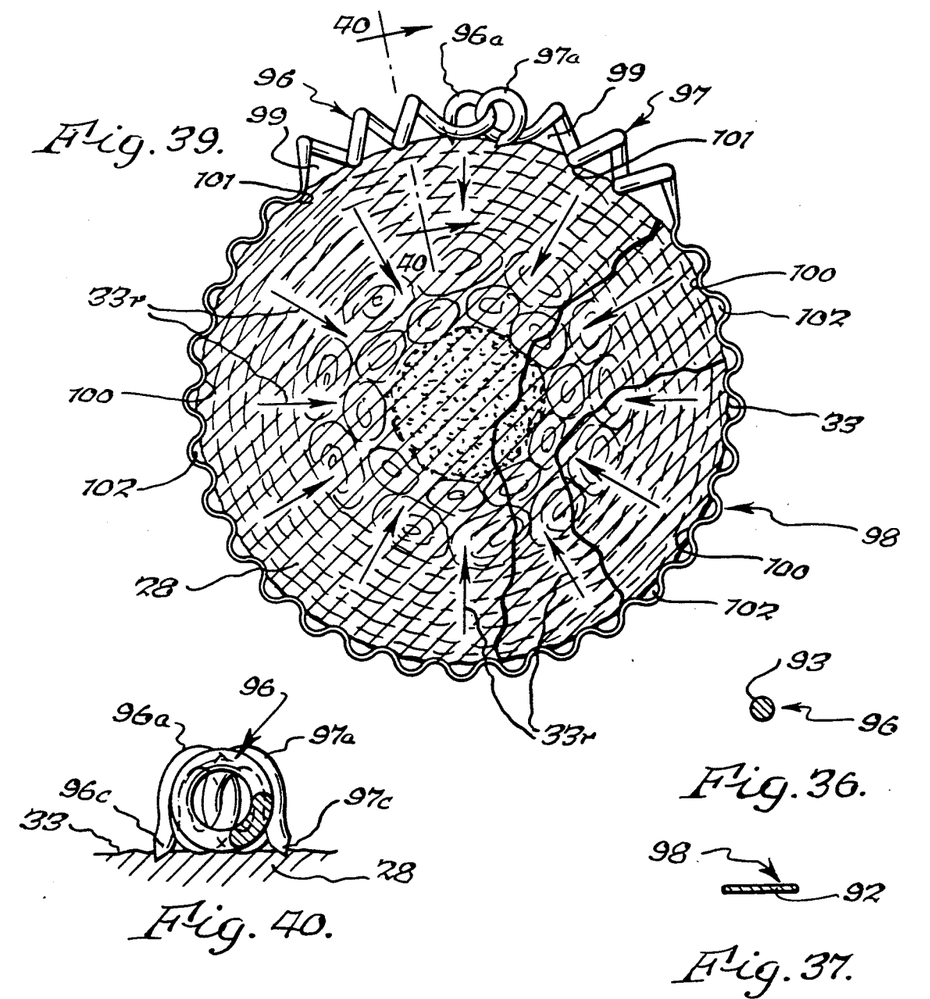
FIG. 36 is an enlarged cross-sectional view taken along line 36—36 of FIG. 35.
FIG. 37 is an enlarged cross-sectional view taken along line 37—37 of FIG. 35.
FIG. 39 is a cross-sectional view of a fragmented bone bound by the suture of FIG. 38 and having its ends hooked together in a tensioned condition.
FIG. 40 is a cross-sectional view taken along line 40—40 of FIG. 39.
Figure 38:
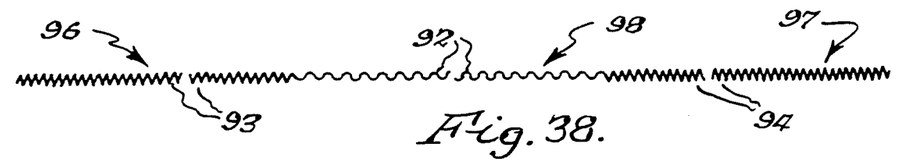
FIG. 38 is a side elevational view of the device shown in FIG. 35 having each of its round ends wound into continuous helical coils and its middle portion corrugated.
Figure 41:
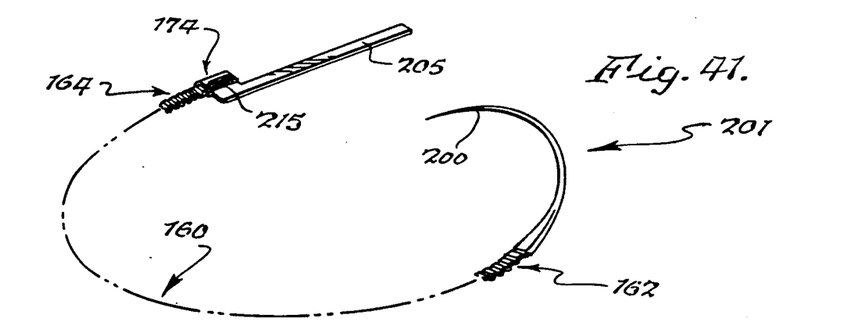
FIG. 41 is a fragmentary perspective view of a modified suture having a locking clip with a pull tab at one end and a needle at its other end.
Figure 42:
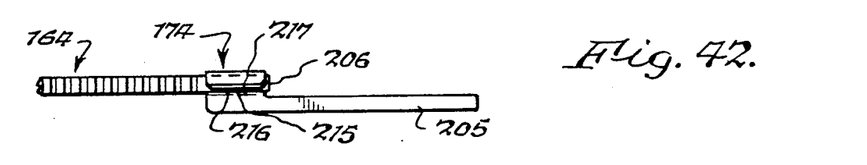
FIG. 42 is a top plan of the locking clip and pull tab end.

In the form of the invention shown in FIGS. 35-40 a monofilament length of surgical wire 91 is provided with a flattened middle portion 92 shown in cross section in FIG. 37 and a first end 93 and a second end 94, both of which are wire in cylindrical cross section as seen in FIG. 36. This length of wire is then coiled at its first end 93 into continuous coils 96 and at its second end 94 into continuous coils 97 while its middle portion 92 is worked into a corrugated section 98.

All coils 96 and 97 and segment 98 are elastic by their nature and will also elongate when stretched beyond their elastic limit. Middle portion 98 has broad bone contacting areas 100 with void spaces 102 therebetween while the coiled sections 96 and 97 also have a wide tread 101, and void spaces 99. Hooked coils 96a and 97a are used to hold the suture ends 96 and 97 together and are equivalent to those identified as 26y, 26y and 30c, 31c and as previously described and shown in FIG. 18.

A suture 201 shown in FIGS. 41-47 is comprised of a corrugated monofilament similar to that illustrated in FIGS. 1, 14 and 15 previously described. The suture 201 has a first end 162, a middle portion 160 and a second end 164. The corrugations are a uniform series of bone contact points 166 on their contact side which on their back sides form receptors 168 for the points 166. Voids or spaces 167 form passages for flow of materials from one side to the other of the suture 201 when installed around a bone, see FIG. 47.

Figure 43:
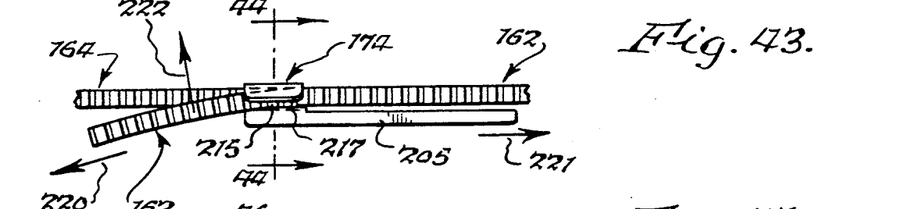
FIG. 43 is a similar view with its opposite end being entered into the clip.
Figures 44, 45, 46:
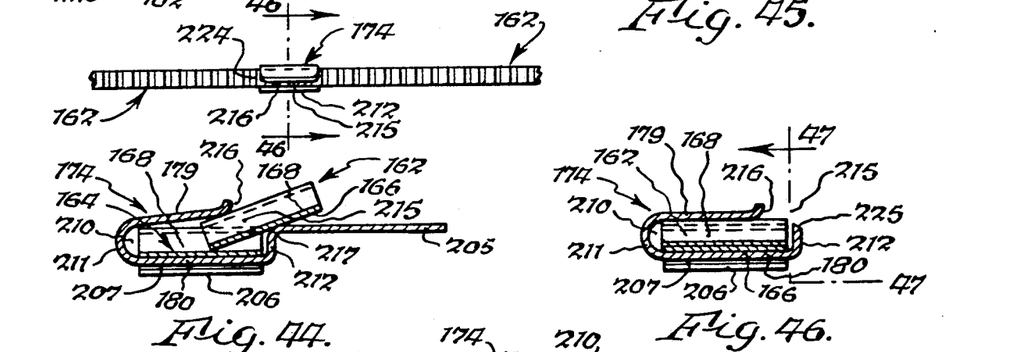
FIG. 44 is a cross-sectional view taken along line 44—44 of FIG. 43.
FIG. 45 is a fragmentary plan view similar to FIGS. 42 and 43 with the opposite end of the band locked into the clip and trimmed of the excess ends.
FIG. 46 is a cross-sectional view taken along line 46—46 of FIG. 45 showing the opposite end locked in the clip.
Figure 47:
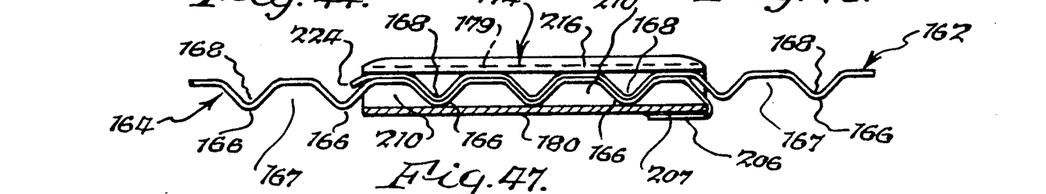
FIG. 47 is a linear cross-sectional view taken along line 47—47 of FIG. 46, showing the opposite ends of the band in a locking interspersing of each other embraced by the clip to maintain the tension in the suture.

Formed integrally with or affixed thereto may be a needle 200 to the first end 162 while the second end 164 may carry a retaining clip 174. Said clip 174 is of a C shaped conformation having a top leg 179 with a bottom leg 180 connected by a vertical wall bend 211 and a vertical front wall 212 connected at its upper end by a bend 217 to a pull tab 205. A space 215 formed by the bend 217 and a flare 216 of the top leg 179 forming a throat 215 for the entrance of the first end 162 when the suture is being wrapped around a bone 28 as in FIG. 1. The first end 162 is layed upon the pull tab 205 and tension is applied as indicated by arrows 220 and 221 to tighten the suture 201 as seen in FIG. 43. As the contact points 166 of end 162 register with the receptors 168 of end 164 this end 164 is entered into the throat 215 of the clip 174 as indicated by the arrow 222 in FIG. 43 and also seen in the cross sectional view of FIG. 44. It will be seen that the upper leg 179 is flexed upwardly as the end 162 is angled into the clip 174. When insertion is completed as seen in FIGS. 46 and 47 the corrugations 166, 168 become interlocked together against any linear movement to retain the tension in the suture 201.

After locking takes place the tab 205 is trimmed off parallel to the side of the clip 174 and the excess of first end 162 is also trimmed off at 224. The clip 174 may be attached to the second end 164 by any suitable fastening means or material 207 and bent back over the lower leg 180 of the clip 174 shown in FIGS. 44, 45 and 47.

Application of this suture provides a constant pressure that is gentle but firm, to urge separated parts to join and heal together aided and abetted by a free flow of blood, body fluids and nerve channels with a minimal presence of a foreign body.

While preferred embodiments of the present invention have been disclosed, it will be understood that the present invention is not limited thereto, but may be otherwise embodied within the scope of the following claims.

What is claimed is:

1. A method of suturing a longitudinally fractured live bone at a specific circumferential area to maintain it in properly assembled relationship while permitting free communication of blood vessels, nerve channels and body fluids across said specific circumferential area, comprising the steps of providing an elongated flexible sinuous member having bone contacting areas alternating with non-contacting spaces, said non-contacting spaces permitting said communication across said sinuous member, winding said sinuous member about said bone in said circumferential area, tensioning said sinuous member, and securing the end portions thereof to each other to maintain said sinuous member in properly assembled and tensioned relationship on said fractured bone.

* * * * *